(12) United States Patent
Palm

(10) Patent No.: US 7,927,309 B2
(45) Date of Patent: Apr. 19, 2011

(54) EXPANDABLE SHEATH INTRODUCER

(75) Inventor: Mark Erwin Palm, Davie, FL (US)

(73) Assignee: Cordis Corporation, Miami, FL (US)

( * ) Notice: Subject to any disclaimer, the term of this patent is extended or adjusted under 35 U.S.C. 154(b) by 388 days.

(21) Appl. No.: 11/754,564

(22) Filed: May 29, 2007

(65) Prior Publication Data

US 2008/0300544 A1 Dec. 4, 2008

(51) Int. Cl.
*A61M 5/178* (2006.01)
(52) U.S. Cl. ............... 604/164.03; 606/1.13; 606/1.17
(58) Field of Classification Search ............ 604/164.03; 623/1.13, 1.17, 1.23, 1.25
See application file for complete search history.

(56) References Cited

U.S. PATENT DOCUMENTS

| | | | |
|---|---|---|---|
| 4,411,655 A | 10/1983 | Schreck | |
| 4,776,337 A * | 10/1988 | Palmaz | 623/1.11 |
| 4,798,594 A | 1/1989 | Hillstead | |
| 4,895,565 A | 1/1990 | Hillstead | |
| 5,460,170 A | 10/1995 | Hammerslag | |
| 5,628,786 A * | 5/1997 | Banas et al. | 623/1.13 |
| 5,653,697 A * | 8/1997 | Quiachon et al. | 604/528 |
| 5,667,523 A * | 9/1997 | Bynon et al. | 623/1.13 |
| 5,749,880 A * | 5/1998 | Banas et al. | 606/198 |
| 6,080,174 A * | 6/2000 | Dubrul et al. | 606/185 |
| 6,183,443 B1 * | 2/2001 | Kratoska et al. | 604/164.03 |
| 6,228,068 B1 * | 5/2001 | Yoon | 604/246 |
| 6,245,052 B1 | 6/2001 | Orth et al. | |
| 6,270,484 B1 * | 8/2001 | Yoon | 604/264 |
| 6,692,462 B2 | 2/2004 | Mackenzie et al. | |
| 6,758,858 B2 * | 7/2004 | McCrea et al. | 623/1.13 |
| 7,597,775 B2 * | 10/2009 | Sogard et al. | 156/294 |
| 2001/0012946 A1 * | 8/2001 | MacKenzie et al. | 606/185 |
| 2002/0002360 A1 * | 1/2002 | Orth et al. | 604/506 |
| 2004/0199121 A1 * | 10/2004 | Wenchell et al. | 604/167.06 |
| 2005/0080430 A1 * | 4/2005 | Wright et al. | 606/108 |
| 2005/0131515 A1 * | 6/2005 | Cully et al. | 623/1.13 |

* cited by examiner

Primary Examiner — Nicholas D Lucchesi
Assistant Examiner — Gerald Landry, II
(74) Attorney, Agent, or Firm — Cook Alex Ltd.

(57) ABSTRACT

The disclosure relates to an a catheter sheath introducer that is capable of being expanded from first diameter to second diameter in order to accommodate differently sized medical devices to be introduced by the sheath introducer. The device is structured such that it does not foreshorten when expanded.

14 Claims, 2 Drawing Sheets

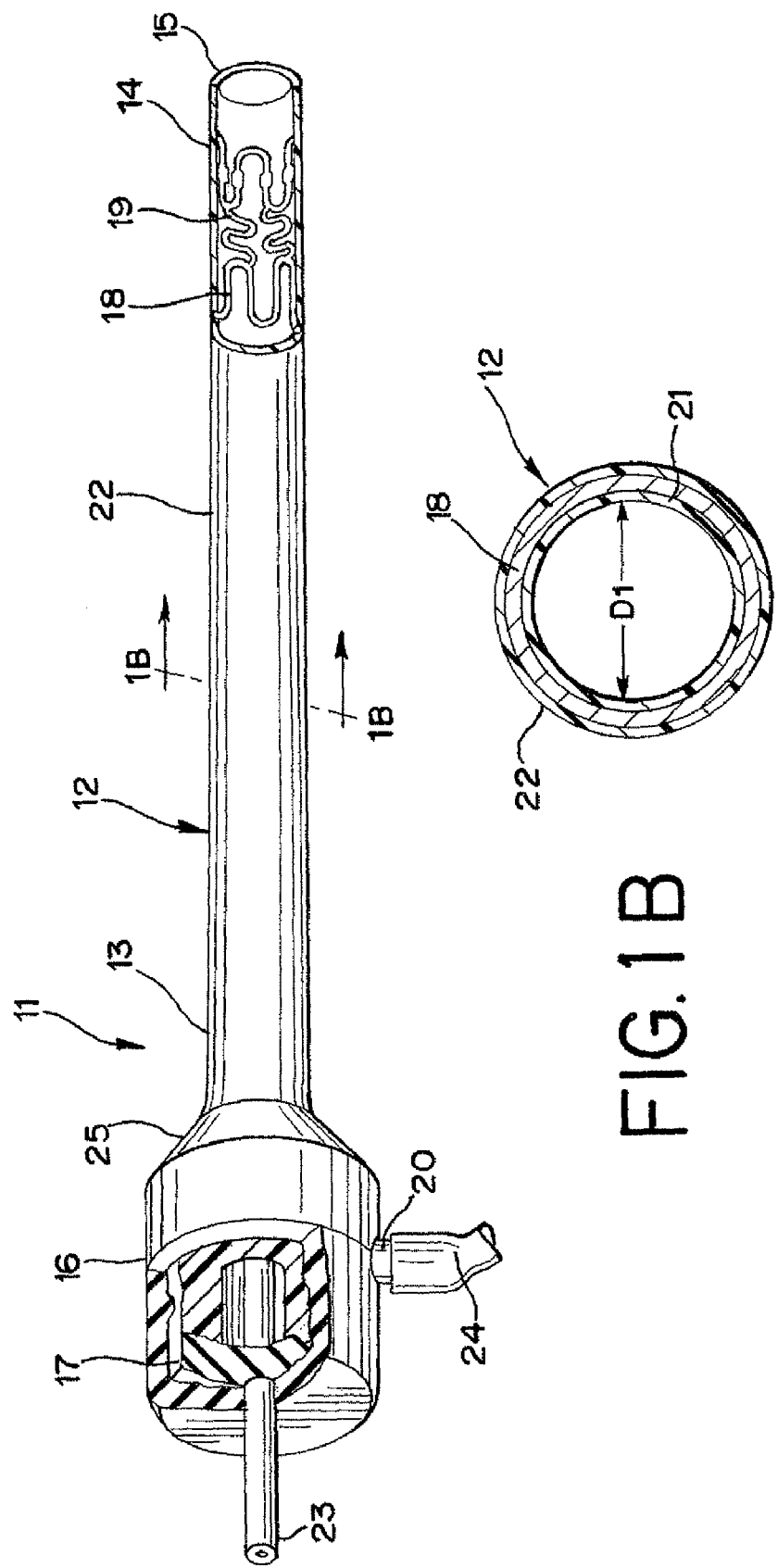

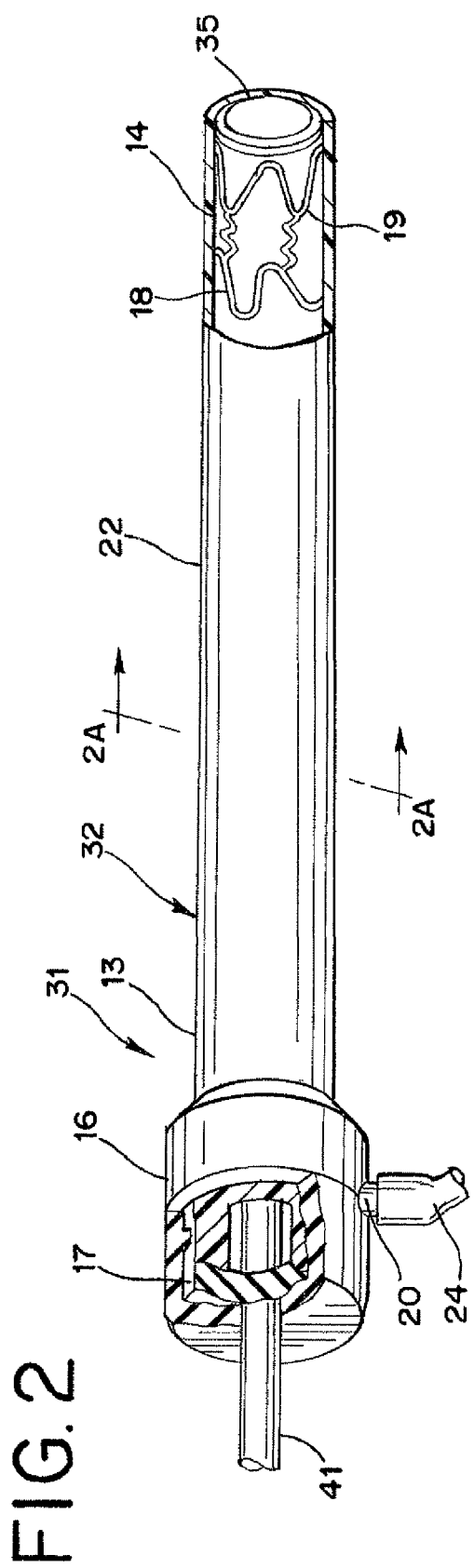
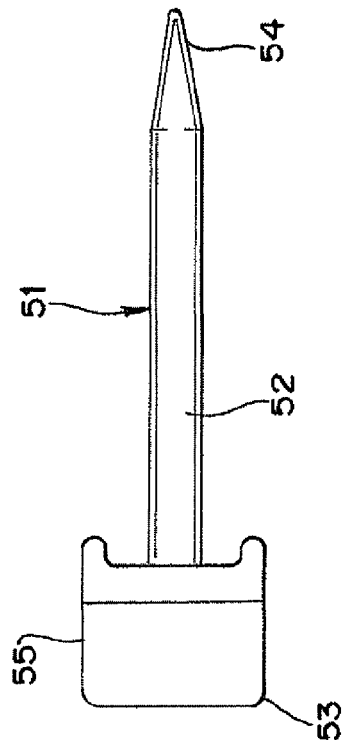
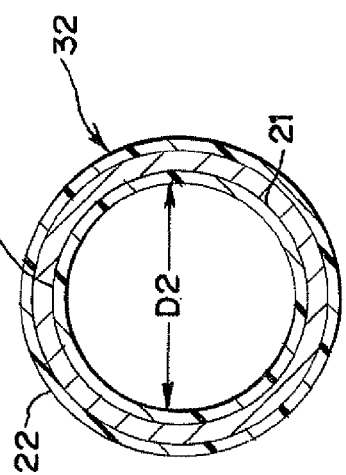

EXPANDABLE SHEATH INTRODUCER

FIELD OF THE INVENTION

This disclosure relates to introducers used for placing medical devices, including catheters, into a patient. More particularly, this relates to introducers that minimize the need to exchange introducers during a medical procedure.

BACKGROUND OF THE DISCLOSURE

In some medical procedures, tubular structures such as sheath introducers are inserted into tissue to allow access to a particular body structure, and medical devices are then passed through the tubular structure to a desired site. For example, a catheter may be passed through a sheath introducer to place the catheter into the vasculature of a patient as a step in a catheter-based medical procedure.

In one common situation, a physician will often first perform a diagnostic procedure using a relatively narrow-diameter diagnostic device which requires a correspondingly narrow-diameter sheath introducer. To insert a larger-diameter interventional device, the physician may need to replace the narrow diameter sheath introducer with one that can accommodate the interventional device, resulting in a large number of manipulations that may lead to complications.

U.S. Pat. No. 6,692,462, herein incorporated by reference, describes a radially expandable sleeve for allowing access to the vasculature. The sleeve can be expanded from a narrow to a wide diameter as required. However, the described device of this reference would undergo foreshortening when it expands. That is, the overall length of the sleeve would be reduced when it is in the expanded position.

The present disclosure recognizes that foreshortening in a sleeve or similar structure may have several detrimental effects. For example, the materials from which the sleeve is manufactured may fold or ripple, thereby rubbing and agitating the surrounding tissue and possibly initiating spasm. Foreshortening may also complicate the placement of the sleeve and therefore the accurate placement of the medical device.

Prior art of this type does not disclose, suggest or teach an approach to reduce manipulations between introducers of different diameters or sizes, such as by providing one sheath introducer that could accommodate a range of differently sized medical devices, especially a sheath introducer that can be used to accommodate medical devices of different sizes and which does not undergo foreshortening when it expands.

SUMMARY

This disclosure relates to a sheath introducer which includes a hub and a tube with a lumen. The tube may be expanded from a first inner diameter to a second inner diameter without foreshortening during expansion. Typically, the tube is formed in three radially spaced and longitudinally extending layers. The middle layer of such a tube construction has stent-like properties.

The disclosure also relates to a method of using a sheath introducer where the sheath introducer is positioned in the body of a patient such that its proximal end is accessible to a medical professional and its distal end is positioned to allow a medical device to be inserted at a desired location in the patient. The sheath introducer includes a tube that may be expanded from a first inner diameter to a second inner diameter without foreshortening during expansion.

The disclosure also relates to a method for making and using a tube of a sheath introducer that does not foreshorten when it is expanded.

BRIEF DESCRIPTION OF THE DRAWINGS

FIG. 1A is a perspective view of a sheath introducer according to the disclosure in its first (unexpanded) diameter and with portions cut away to show internal features;

FIG. 1B is a cross-sectional view along the line 1B-1B of FIG. 1;

FIG. 2 is a perspective view of the sheath introducer of FIGS. 1A and 1B that has been opened to a second (expanded) diameter and with portions cut away to show internal features;

FIG. 2A is a cross-sectional view along the line 2A-2A of FIG. 2; and

FIG. 3 is an elevational view of a dilator that can be used with the embodiments of the sheath introducer of the disclosure.

DESCRIPTION OF THE PREFERRED EMBODIMENTS

As required, detailed embodiments are disclosed herein; however, it is to be understood that the disclosed embodiments are merely exemplary. Therefore, specific details disclosed herein are not to be interpreted as limiting, but merely as a basis for the claims and as a representative basis for teaching one skilled in the art to variously employ the disclosure in virtually any appropriate manner.

A sheath introducer according to the disclosure may be used to insert a medical device into blood vessels as well as other tissues. An embodiment of a sheath introducer 11 encompassed by the present disclosure is shown in FIG. 1A and FIG. 1B in its unexpanded position and with sections cut away to show internal features. The introducer 11 includes a tube 12 with proximal end portion 13 and distal end portion 14. The tube contains a lumen 15 with a first inner diameter D1 that is an unexpanded diameter. A hub 16 is attached to the proximal end 13 of the tube. The hub is designed to allow entrance of a medical device 23 to the tube.

The proximal end 13 of the tube may be flared to a greater diameter than the rest of the tube so that the tube may be fitted onto the hub 16 at a tapered portion 25. This flaring can be formed by any suitable approach. Tapered portion 25 can be provided upon molding or other manner of forming the tube and/or hub. Tapered portion 25 can be provided by a shaping operation such as swaging, for example. In a further embodiment, the hub includes a hemostasis valve 17. A sideport 20 with attached tubing 24 may also be included so that fluid may be introduced into the sheath introducer. Hemostasis valves are well-known in the art and examples are disclosed in U.S. Pat. No. 4,798,594 and No. 4,895,565 which are herein incorporated by reference.

The tube 12 that is illustrated is formed from three layers. In this and further embodiments, a component is included that functions as an expander layer 18 that typically has a structure with stent-like properties in that the expander layer will expand radially when the sheath introducer 11 is subjected to an outwardly directed radial force to expand its inner diameter. For example, the expander layer 18 may have a mesh-like structure 19 similar to that used in many stent designs. As with stents, the present expander layer is capable of being expanded radially from a first diameter to a second diameter. The expander layer design is such that it substantially maintains its longitudinal extent whether expanded radially or unexpanded. Thus, when expanded radially, the expander layer 18 will not foreshorten. With this characteristic of the expander layer 18, the sheath introducer likewise will not foreshorten.

It is generally the case that the expander layer 18 is between and typically substantially encapsulated within and between components that typically enhance exterior smoothness of the expander layer 18. Such can be accomplished by providing an interior layer defining the introducer lumen, at times referred to herein as the inner layer 21, as well as an exterior layer defining the outside surface of the sheath introducer, at times referred to herein as the outer layer 22.

The inner layer 21 and outer layer 22 of the tube 12 may be formed from materials that are expandable and that are biocompatible. In one embodiment, the inner and outer layers are formed from the same material. Each of the inner layer and outer layer preferably is formed from a material, whether the same or different, that, in cooperation with the non-foreshortening characteristic of the expander layer 18 does not readily fold or form ripples when the introducer is introduced and manipulated. In this way, irritation of tissue is minimized, thereby providing an important and advantageous feature.

It has been found that the inner and outer layers can be suitably manufactured from a polymer having a hardness between about 20 A and about 70 D, typically between about 40 A and about 50 D, or between about 70 A and about 30 D. An example is a polyether polyamide copolymer having a hardness of from between about 20 A and about 70 D, typically between about 40 A and about 50 D, or between about 70 A and about 30 D. Lubricity enhancement can be achieved by including a lubricity agent such as PTFE (polytetrafluoroethylene). An example is a PTFE-filled PEBAX-type of resin. In FIG. 2 the sheath introducer is shown as an expanded introducer 31 with hub 16 as in FIG. 1A according to the disclosure. The tube has been expanded into an expanded tube 32 with proximal end 33 and distal end 34. Tube 32 has a lumen with a second inner diameter, D2 that is larger than diameter D1. In this embodiment, a medical device 41 having a larger diameter than medical device 23 may be inserted than is possible at the unexpanded state of the sheath introducer as shown at 11 in FIG. 1A. The expansion from the tube 12 at the unexpanded state to the tube 32 at the expanded state of this illustrated embodiment is accomplished through expansion of the stent-like expander layer to an expanded layer 38 and the inner layer 39 and outer layer 40 such that the tube length does not foreshorten or otherwise change in length during expansion radially to accommodate the larger medical device without having to remove a small-diameter introducer and deploy a different, larger-diameter introducer.

Examples of stent designs that do not foreshorten when expanded and which are compatible with the present disclosure include but are not limited to those that are manufactured by Cordis Corporation (e.g. BX VELOCITY® stent), Boston Scientific corporation (e.g. EXPRESS® stent), Conor Medsystems LLC (e.g. Co-Star™ stent), Abbott Corporation (e.g. XIENCE™ stent) and Medtronic Incorporated (e.g. DRIVER® stent).

The stent-like structure for the expander layer 18 may be formed from a number of materials used in the manufacture of stents. Stainless steel is one commonly used material. The structure may be formed from shape memory metals such as nickel-titanium alloys (e.g. nitinol alloys) and cobalt-chromium alloys, although this is not necessary. Shape memory materials can provide a super-elastic characteristic.

According to one embodiment, a sheath introducer of the disclosure may be used by inserting a needle into a patient and a guide wire is fed through the needle to the desired location. After removal of the needle, the sheath introducer with dilator is inserted over the guide wire and guided to a site where the distal end of the sheath introducer lies within the desired tissue location, such as the vasculature. The dilator is removed, and the proximal end of the sheath introducer remains accessible to the medical professional. In a first diameter such as diameter D1, a catheter or other medical device may be introduced through the sheath introducer to the desired location in the body.

To expand the sheath introducer to a second diameter, such as D2, a larger diameter dilator of a type used to expand tissue may be inserted in the sheath introducer. FIG. 3 shows an example of such a dilator 51. The dilator includes a shaft 52 with a proximal end 53 and a distal 54 end, a handle 55 being attached to the proximal end. The dilator is introduced through the proximal end of the unexpanded sheath introducer into the lumen of the tube and is capable of expanding the diameter of the sheath introducer such that it may accommodate a medical device with a larger diameter. The expansion in diameter can be to the extent of about 1 French to about 3 French, for example, or as otherwise required, beyond the unexpanded diameter D1. For example, the sheath introducer may be able to accommodate a diagnostic catheter of about 4 French in its first or unexpanded diameter and may accommodate a second catheter of up to 7 French when expanded to its second or expanded diameter position. However, a sheath introducer of the disclosure may be designed for and employed in numerous situations that require the introduction of medical devices of various sizes.

According to one embodiment, the tube for a sheath introducer according to the disclosure may be manufactured by a procedure including extruding polymer over a wire or mandrel to form inner layer 21. Then the expander layer 18 is placed over the inner layer, and a polymer is extruded over the expander layer 18 to provide the outer layer 22. In this illustrated embodiment, the inner and outer layers are bonded to each other. In one embodiment, the expander layer may be crimped to the inner layer, typically prior to extruding the outer layer thereover. In another embodiment, the expander layer may be sized such that it fits onto the inner layer without a need for crimping or similar procedure. As described above, the tube may be swaged to fit onto a hub.

It will be understood that the embodiments which have been described are illustrative of some of the applications of the principles of the disclosure. Numerous modifications may be made by those skilled in the art without departing from the true spirit and scope of the disclosure. Various features which are described herein can be used in any combination and are not limited to procure combinations that are specifically outlined herein.

The invention claimed is:

1. A sheath introducer for accommodating a plurality of elongated medical devices of different respective outer diameters, the sheath introducer, comprising
   a hub;
   a tube assembly secured to the hub, wherein said tube assembly permits radial expansion thereof, resists radial collapse thereof, and comprises:
   (a) an inner layer that is an extruded polymer tube that permits radial expansion but does not resist radial collapse;
   (b) an expander layer, the expander layer comprised of a stent-like mesh structure that permits radial expansion and resists radial collapse while same substantially maintains its longitudinal extent and does not foreshorten when same is expanded radially when subjected to an outwardly directed radial force;

(c) an outer layer that is an extruded polymer tube that permits radial expansion but does not resist radial collapse;

(d) said inner layer, said expander layer and said outer layer are separate layers assembled into said tube assembly, said expander layer being positioned between said inner layer and said outer layer;

(e) said inner and outer layers are made of the same or different polymer, each having a Shore durometer hardness of from about 20 A to about 70 D; and said tube assembly radial expansion is from a first, unexpanded diameter to a second, expanded diameter and does not fold or form ripples therein due to foreshortening of the expander layer when said tube thus expands.

2. The sheath introducer of claim 1, wherein said expander layer is formed from a material selected from the group consisting of stainless steel, nickel-titanium alloys, cobalt-chromium alloys, and combinations thereof.

3. The sheath introducer of claim 1, wherein said expander layer is formed from stainless steel.

4. The sheath introducer of claim 1, wherein said inner and outer layers are formed from the same material.

5. The sheath introducer of claim 1, wherein said inner and outer layers are formed from materials selected from the group consisting of polyamide polyether copolymers, lubricious polyamide polyether copolymers, polytetra-fluoro-ethylene filled copolymers, and combinations thereof.

6. The sheath introducer of claim 1, wherein said inner and outer layers are formed from a PEBAX copolymer.

7. The sheath introducer of claim 1, wherein the Shore durometer hardness is from about 70 A to about 30 D.

8. The sheath introducer of claim 1, wherein the expansion in diameter from said first diameter to said second diameter is an expansion of about 0.1 French to about 3 French.

9. The sheath introducer of claim 1, wherein said first, unexpanded diameter is adequate to allow passage of a diagnostic catheter through the introducer, wherein said second, expanded diameter is adequate to allow passage of a interventional catheter through the introducer, and said expansion exhibits a reduced risk of spasm of tissue in contact with the sheath introducer.

10. The sheath introducer of claim 1, further comprising a hemostasis valve.

11. A method of making a sheath introducer, comprising:
providing an expandable tube assembly by a procedure including:
a) extruding an inner polymeric layer over a mandrel to form a tube that permits radial expansion but does not resist radial collapse;
b) positioning an expander layer over the inner layer, the expander layer has stent-like properties, is comprised of a mesh structure, permits radial expansion, resists radial collapse, substantially maintains its longitudinal extent, and does not foreshorten when same is radially expanded;
c) extruding an outer polymeric layer over said expander layer to form a tube that permits radial expansion but does not resist radial collapse;
securing an introducer hub to the expandable tube assembly; and
said providing of the expandable tube assembly results in the expandable tube assembly having the property of not folding or forming ripples therein due to foreshortening of the expander layer when said tube is radially expanded while the expander layer imparts to the tubing assembly the property of resisting radial collapse.

12. The method of claim 11, wherein the expander layer is crimped to the inner layer.

13. The method of claim 11, further including bonding the inner layer to the outer layer with the expander layer therebetween.

14. A method of using a sheath introducer for introducing medical devices of respective different diameters, comprising:
providing a sheath introducer having a lumen expandable from a first diameter to a second diameter larger than the first diameter, the sheath introducer having a tube assembly of an inner layer tube and outer layer tube, and the inner and outer layer tubes each are radially expandable while not resisting radial collapse and are made of the same or different polymer, each having a Shore durometer hardness of from about 20 A to about 70 D, the sheath introducer including an expander layer between the inner and outer layers that is comprised of a stent-like mesh structure that permits radial expansion and resists radial collapse and substantially maintains its longitudinal extent and does not foreshorten when same is radially expanded;
a) positioning the sheath introducer with the lumen at the first lumen diameter such that the proximal end of said sheath introducer is accessible to a medical professional and the distal end of said sheath introducer is within a desired site of the body;
b) inserting one medical device having a given outer diameter into the body through the sheath introducer at the first lumen diameter;
c) dilating by inserting a dilator into said sheath introducer causing an expansion to the second diameter without ripples therein due to foreshortening of the expander layer when the sheath introducer is thus dilated;
d) inserting another medical device into the body through the sheath introducer without removing the sheath introducer from the body, said another medical device having an outer diameter greater than said given outer diameter and greater than said first lumen diameter; and
e) said dilating expands the sheath introducer from the first lumen diameter to the second lumen diameter without folding or forming ripples therein due to expander layer foreshortening and thus reduces risk of spasm of body tissue in contact with the sheath introducer during said dilating and during said introducing of another medical device.

* * * * *